United States Patent
Hougee et al.

(10) Patent No.: US 9,456,629 B2
(45) Date of Patent: Oct. 4, 2016

(54) NUTRITION WITH NON-VIABLE BIFIDOBACTERIUM AND NON-DIGESTIBLE OLIGOSACCHARIDE

(75) Inventors: Sander Hougee, Driebergen-Rijsenburg (NL); Adrianus Johannes Maria Vriesema, Houten (NL); Johan Garssen, Nieuwegein (NL); Jan Knol, Wageningen (NL)

(73) Assignee: N.V. NUTRICIA, Zoetermeer (NL)

( * ) Notice: Subject to any disclaimer, the term of this patent is extended or adjusted under 35 U.S.C. 154(b) by 1140 days.

(21) Appl. No.: 12/664,785

(22) PCT Filed: Jun. 13, 2008

(86) PCT No.: PCT/NL2008/050376
§ 371 (c)(1),
(2), (4) Date: Jun. 14, 2010

(87) PCT Pub. No.: WO2008/153391
PCT Pub. Date: Dec. 18, 2008

(65) Prior Publication Data
US 2010/0278781 A1 Nov. 4, 2010

(30) Foreign Application Priority Data
Jun. 15, 2007 (WO) ................ PCT/NL2007/050290

(51) Int. Cl.
| | |
|---|---|
| A61K 39/39 | (2006.01) |
| A23L 1/30 | (2006.01) |
| A23L 1/09 | (2006.01) |
| A23L 1/29 | (2006.01) |
| A23L 1/308 | (2006.01) |
| A61K 31/702 | (2006.01) |
| A61K 31/733 | (2006.01) |
| A61K 35/745 | (2015.01) |

(52) U.S. Cl.
CPC ................ *A23L 1/3014* (2013.01); *A23L 1/09* (2013.01); *A23L 1/296* (2013.01); *A23L 1/3008* (2013.01); *A23L 1/308* (2013.01); *A23L 1/3081* (2013.01); *A61K 31/702* (2013.01); *A61K 31/733* (2013.01); *A61K 35/745* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 5,602,109 A | * | 2/1997 | Masor et al. | ................ 514/45 |
| 6,436,464 B1 | * | 8/2002 | Euber | ........................ 426/654 |
| 2003/0157067 A1 | | 8/2003 | Bartels | |

FOREIGN PATENT DOCUMENTS

| | | | | |
|---|---|---|---|---|
| EP | 1629850 A | | 3/2006 | |
| JP | 01242532 A | | 9/1989 | |
| WO | 0008948 A | | 2/2000 | |
| WO | 0113927 A | | 3/2001 | |
| WO | 0113956 A | | 3/2001 | |
| WO | 2004112509 A | | 12/2004 | |
| WO | 2005039319 A | | 5/2005 | |
| WO | 2005058335 A | | 6/2005 | |
| WO | 2005122790 A | | 12/2005 | |
| WO | 2006091103 A | | 8/2006 | |
| WO | WO 2006108824 A1 | * | 10/2006 | ............... A23L 1/29 |
| WO | 2006115412 A | | 11/2006 | |
| WO | 2007046698 A | | 4/2007 | |

OTHER PUBLICATIONS

Heyman et al.,"Effects of specific lactic acid bacteria on the intestinal permeability to macromolecules and the inflammatory condition," ACTA Paediatrica, 2005, pp. 34-36, vol. 94, No. suppl. 449.
F. Longhi, et al., "Diaper dermatitis: a study of contributing factors." Contact Dermatitis 26:248-252 (1992).
B. Schouten et al., "Cow Milk Allergy Symptoms are Reduced in Mice Fed Dietary Synbiotics during Oral Sensitization with Whey," J. Nutrition 139:1398-1403, 2009.

* cited by examiner

*Primary Examiner* — Robert T Crow
(74) *Attorney, Agent, or Firm* — Browdy and Neimark, PLLC

(57) ABSTRACT

An infant and/or toddler nutrition comprising non-viable *Bifidobacterium breve* and a non-digestible oligosaccharide and its use are disclosed.

11 Claims, No Drawings

NUTRITION WITH NON-VIABLE *BIFIDOBACTERIUM* AND NON-DIGESTIBLE OLIGOSACCHARIDE

FIELD OF THE INVENTION

The present invention relates to the field of infant and/or toddler nutrition. In particular the present invention relates to an infant and/or toddler nutrition with non-digestible oligosaccharide and non-viable bifidobacteria. Such a nutritional composition is advantageously used to treat or prevent allergy, preferably food allergy, and/or atopic diseases including atopic dermatitis and/or asthma.

BACKGROUND OF THE INVENTION

A human infant fed human milk will develop after birth an intestinal microbiota rich in lactic acid producing bacteria. This is due to the presence of non-digestible saccharides in human milk which are specifically fermented by lactic acid producing bacteria, especially bifidobacteria.

A microbiota rich in bifidobacteria is beneficial since it has a preventive effect on infections, diarrhoea, constipation, gastro-intestinal inflammation, intestinal maturation, allergy, in particular food allergy, atopic diseases including atopic dermatitis, and asthma and it has a beneficial effect on the immune system.

Formula for young children can be adapted to mimic the bifidogenic effect of human milk. WO 2005039319 discloses the use of living *Bifidobacterium breve* and a mixture of two different non-digestible saccharides to improve the microbiota of formula fed infants. The document discloses the relevance of bifidobacteria on a genus level as well as on a species level. WO 20070046698 discloses the use of a composition comprising non-digestible oligosaccharide for the manufacture of a composition for enteral administration to an infant delivered via caesarean section. Live lactic acid bacteria are to be co-administered to increase the diversity and/or the quantity of microorganisms in the intestine of the caesarean delivered infant. JP 01242532 discloses the use of viable or non-viable *B. breve* as an immunopotentiator that stimulates Peyer's patches thereby preventing intra-intestinal tract infection and allergy. This document does not concern nutritional formula for infants and/or toddlers.

SUMMARY OF THE INVENTION

It is known that living *B. breve* cells can improve the microbiota and thereby improve allergy. However, the use of non-viable *B. breve* is preferred. This has several advantages:

1) A product comprising non-viable *B. breve* can be stored more easily and with reduced costs, since no special precautions have to be taken to maintain the viability of *B. breve* cells at an acceptable level. This is especially the case in products with a water activity above 0.3.
2) No post-acidification occurs due to the absence of fermentative capability of *B. breve* in stored products with a high water activity and/or in infant formula in the period after reconstitution with water and before consumption.
3) After production, the final nutritional composition with non-viable *B. breve* can be pasteurized and/or sterilized, consequently reducing the chance on contamination with harmful micro-organisms, such as *E. sakazakii*. So the present invention enables liquid, ready-to-use formula comprising non-viable *B. breve* to be prepared and stored at room temperature.
4) A powdered product with non-viable *B. breve* can be reconstituted with water with a temperature above 37° C., if desired.
5) The dose of *B. breve* cells received by each infant and/or toddler can be more easily controlled, since no further growth in a liquid product occurs, nor growth in the intestinal tract of the infant. The latter is a variable factor depending on the individual's intestinal environment, and thereby leads to variations in the extent of beneficial effects in individual infants.

The inventors have surprisingly found that infant and/or toddler nutrition comprising non-digestible oligosaccharides can be advantageously supplemented with non-viable *Bifidobacterium breve* cells to have a preventive and/or curative effect on food allergy and/or other atopic diseases. The effect of non-viable *Bifidobacterium breve* in compositions was comparable to that of viable *B. breve* cells. The observed anti-allergic effect of inactivated *B. breve* cannot be explained by a direct probiotic effect, such as an effect via improvement of the flora, since the cells are no longer living and therefore do not increase the number of *B. breve* cells in the microbiota. So far, the beneficial effects of *B. breve* were presumed to be dependent on the presence of living cells.

The effect of non-viable *B. breve* cells was comparable, but slightly smaller than that of living *B. breve*. The present inventors have surprisingly found that the effect of non-viable *B. breve* could even be further improved by the presence of non-digestible oligosaccharides. This is unexpected, since generally in synbiotic preparations the present non-digestible oligosaccharide stimulate the present probiotic bacteria and thereby show an improved effect. The inventors have unexpectedly found that also in preparations comprising inactivated *B. breve*, which is not able to use and benefit from the present non-digestible oligosaccharides, also an improved effect was found of the combination compared to the single compounds.

The non-digestible oligosaccharides stimulate the intestinal microbiota of the infant and/or toddler, especially the amount of bifidobacteria and/or lactobacilli. The simultaneous improvement of the microbiota by non-digestible oligosaccharides of formula fed infants and/or toddlers, while administering non-viable *B. breve*, results in an enhanced effect on prevention and/or treatment of disorders such as a preventive effect on infections, diarrhoea, constipation, gastro-intestinal inflammation, intestinal maturation, allergy, particularly food allergy, atopic dermatitis, and/or asthma.

DETAILED DESCRIPTION OF THE INVENTION

The present invention relates to an infant and/or toddler nutrition comprising a non-digestible oligosaccharide A and/or B and an amount of non-viable *Bifidobacterium breve* equivalent to at least $10^3$ cfu per g dry weight of the infant and/or toddler nutrition, and comprising an amount of viable *Bifidobacterium breve* of less than $10^3$ cfu per g dry weight of the infant and/or toddler nutrition.

In one aspect the present invention concerns a method to feed an infant and/or toddler. In a further aspect the present invention concerns a method to treat and/or prevent allergy, preferably food allergy, and/or atopic diseases including atopic eczema and/or asthma, said method comprising administering the present infant and/or toddler nutrition to a subject. In still a further aspect of the present invention concerns a method to treat and/or prevent infection, said method comprising administering the present infant and/or toddler nutrition to a subject.

In still a further aspect of the present invention concerns a method to treat and/or prevent diaper dermatitis, said method comprising administering the present infant and/or toddler nutrition to a subject.

In other words the present invention concerns the use of the present infant and/or toddler nutrition for the manufacture of a composition or nutrition for the treatment and/or prevention of allergy, preferably food allergy, atopic diseases including atopic eczema and/or asthma, or in other words the present invention concerns the present infant and/or toddler nutrition for the use in the treatment and/or prevention of allergy, preferably food allergy, atopic eczema and/or asthma.

Also alternatively worded, the present invention concerns the use the of the present infant and/or toddler nutrition for the manufacture of a composition or nutrition for the treatment and/or prevention of infection, or in other words the present invention concerns the present infant and/or toddler nutrition for the use in the treatment and/or prevention of infection.

Also alternatively worded, the present invention concerns the use the of the present infant and/or toddler nutrition for the manufacture of a composition or nutrition for the treatment and/or prevention of diaper dermatitis, or in other words the present invention concerns the present infant and/or toddler nutrition for use in the treatment and/or prevention of diaper dermatitis.

Bifidobacterium breve

Bifidobacterium breve is a Gram-positive, anaerobic, branched rod-shaped bacterium. The present B. breve preferably has at least 95% identity with the 16 S rRNA sequence when compared to the type strain of B. breve ATCC 15700, more preferably at least 97% identity (Stackebrandt & Goebel, 1994, Int. J. Syst. Bacteriol. 44:846-849). The Bifidobacterium included in the composition and methods and uses of the present invention preferably hybridises with the B. breve probe and gives a signal with the 5' nuclease assay method as described in WO 2005039319.

Preferred B. breve strains are those isolated from the faeces of healthy human milk-fed infants. Typically, these are commercially available from producers of lactic acid bacteria, but they can also directly be isolated from faeces, identified, characterised and produced. According to a preferred embodiment, the present composition contains at least one B. breve selected from the group consisting of B. breve Bb-03 (Rhodia/Danisco), B. breve M-16V (Morinaga), B. breve R0070 (Institute Rosell, Lallemand), B. breve BR03 (Probiotical), B. breve BR92) (Cell Biotech) DSM 20091, and LMG 11613. Most preferably, the non-viable B. breve is non-viable B. breve M-16V (Morinaga). Most preferably, the non-viable B breve is from strain B. breve I-2219 deposited at the CNCM in Paris, France.

The present composition comprises an amount of non-viable Bifidobacterium breve equivalent to at least $10^3$ cfu per g dry weight of the composition. The present composition preferably comprises non-viable B. breve in an equivalent of $10^3$ to $10^{13}$ colony forming units (cfu) B. breve per gram dry weight of the present composition, preferably $10^4$ to $10^{12}$, more preferably $10^5$ to $10^{11}$, most preferably the equivalent of $10^5$ to $10^{10}$ cfu B. breve per gram dry weight of the present composition. Preferably, the present composition comprises non-viable B. breve in an equivalent of $10^4$ to $10^{13}$, more preferably from $10^5$ to $10^{12}$, most preferably the equivalent of $10^6$ to $5 \times 10^{11}$ colony forming units (cfu) B. breve per g of the total of non-digestible oligosaccharide. The dose of non-viable B. breve according to the present invention is preferably administered at a daily dose of the equivalent of $10^4$ to $10^{14}$, more preferably from $10^5$ to $10^{13}$, even more preferably the equivalent of $10^6$ to $10^{12}$, most preferably $10^8$ to $5 \times 10^{11}$ colony forming units (cfu). When the composition is a liquid, the composition preferably comprises the equivalent of $10^4$ to $10^{14}$ colony forming units (cfu) of non-viable B. breve per 100 ml of the present composition, preferably $10^5$ to $10^{13}$, more preferably $10^6$ to $10^{12}$, most preferably the equivalent of $10^6$ to $10^{11}$ cfu B. breve per 100 ml of the present composition.

An amount of non-viable Bifidobacterium breve equivalent to at least $10^3$ cfu per g dry weight means non-viable Bifidobacterium breve in an amount which is the equivalence of an amount of at least $10^3$ cfu B. breve per g dry weight.

The equivalent of cfu can be determined by performing the 5'nuclease assay with the B. breve probes and primers as disclosed in WO 2005039319 in the product (i.e. an infant formula) comprising non-viable B. breve and compare this with a calibration curve obtained from a comparable product (for instance a standard infant formula) to which known amounts of dried, viable B. breve cfu have been added. The dried viable bifidobacteria can be commercially obtained as described above. The value of cfu in the calibration curve made by viable or living B. breve which has the same 5'nuclease assay response as the product comprising the inactivated B. breve is considered to be the equivalent amount in cfu of non-viable B. breve. Alternatively, the amount of cfu per g dry weight can be determined in a composition just before the inactivation step.

The presence of a high amount of viable bifidobacteria would still result in post-acidification in liquid infant formulae. The present composition therefore comprises less than $10^3$ cfu viable bifidobacteria, preferably less than $10^2$, more preferably less than 10 cfu per g dry weight of the composition. When in the form of a liquid, the present composition comprises preferably less than $10^4$ cfu viable bifidobacteria, preferably less than $10^3$, more preferably less than $10^2$ cfu per 100 ml. The cfu of viable bifidobacteria can suitably be determined as described in Ingham, S. C., 1999, J. Food Prot. 62 (1) p. 77-80. Preferably the composition comprises no measurable living B. breve cfu at all. Total absence of living B. breve is however difficult or cannot be determined. Suitably, the absence of living B. breve by plating methods can be determined as being below the detection limit. This detection limit is $10^3$ cfu/g dry weight of composition.

Non-viable B. breve as in the present application relates to dead B. breve, non-culturable B. breve, non-growing B. breve and/or (metabolically) inactive B. breve. B. breve cells can be made non-viable by methods known in the art, including heat treatment steps (including sterilization, pasteurization, UHT treatment), radiation (UV), treatment with oxygen, treatment with bactericidals such as ethanol, sonication, ultra high pressure application, high pressure homogenization and use of a cell disruptor. Preferably the B. breve is heat-killed.

The presence of non-viable B. breve advantageously prevents and/or treats at least one disorder selected from the group consisting of infections, diarrhoea, constipation, gastrointestinal inflammation, disorders caused by impaired intestinal maturation, (food) allergy, atopic dermatitis, eczema, and asthma, while providing many product technological benefits, including increased shelf-life, a reduced incidence of bacterial contamination, decreased post-acidification of the product, improved dosage control and improved convenience of reconstitution.

Non-Digestible Oligosaccharides

The present composition comprises a non-digestible oligosaccharide A and/or B. The non-digestible oligosaccharide A and/or B preferably stimulates the growth of the intestinal lactic acid producing bacteria, particularly bifidobacteria and/or lactobacilli and therefore stimulates the formation of a healthy intestinal microbiota, and preferably is fermented into organic acids. The formed organic acids stimulate mucus production and therefore further improve the intestinal barrier function and/or maturation in infants. Hence, the presence of non-digestible oligosaccharide A and/or B has an advantageous effect on infections, allergy and/or atopic diseases. Advantageously, the non-digestible oligosaccharide A and/or B is water-soluble (according to the method disclosed in L. Prosky et al, J. Assoc. Anal. Chem 71: 1017-1023, 1988) and is an oligosaccharide with a degree of polymerisation (DP) of 2 to 200. The (average) DP of the non-digestible oligosaccharide A and/or B is preferably below 200, more preferably below 100, even more preferably below 60, most preferably below 40. The non-digestible oligosaccharide A and/or B is not digested in the intestine by the action of digestive enzymes present in the human upper digestive tract (small intestine and stomach). The non-digestible oligosaccharide A and/or B is preferably fermented by the human intestinal microbiota. For example, glucose, fructose, galactose, sucrose, lactose, maltose and the maltodextrins are considered digestible. The oligosaccharide raw materials may comprise monosaccharides such as glucose, fructose, fucose, galactose, rhamnose, xylose, glucuronic acid, GalNac etc., but these are not part of the oligosaccharides as in the present invention.

The non-digestible oligosaccharide A and/or B included in the compositions and methods and uses according to the present invention includes a mixture of non-digestible oligosaccharides. This is common practise, because the use of non-digestible oligosaccharide with e.g. one chain length is very expensive. Preferably the non-digestible oligosaccharide is selected from the group consisting of fructo-oligosaccharide (including inulin), non-digestible dextrin, galacto-oligosaccharide (including transgalacto-oligosaccharide), xylo-oligosaccharide, arabino-oligosaccharide, arabinogalacto-oligosaccharide, gluco-oligosaccharide (including gentio-oligosaccharide and cyclodextrin), glucomanno-oligosaccharide, galactomanno-oligosaccharide, mannan-oligosaccharide, chito-oligosaccharide, uronic acid oligosaccharide, sialyloligosaccharide (including 3-SL, 6-SL, LSTa,b,c, DSLNT, S-LNH, DS-LNH) and fuco-oligosaccharide (including (un)sulphated fucoidan OS, 2-FL, 3-FL, LNFP I, II, III, V, LNnFPI, LNDH) and mixtures thereof, more preferably fructo-oligosaccharide (including inulin), galacto-oligosaccharide (including transgalacto-oligosaccharide, α and preferably β linked), uronic acid oligosaccharide and fuco-oligosaccharide and mixtures thereof, even more preferably transgalacto-oligosaccharide and/or inulin, most preferably transgalacto-oligosaccharide. When the non-digestible oligosaccharide A and/or B is a mixture, the averages of the respective parameters are used for defining the present invention.

The present invention preferably provides a composition with two different non-digestible oligosaccharides, i.e. non-digestible oligosaccharide A and non-digestible oligosaccharide B. Non-digestible oligosaccharide A and non-digestible oligosaccharide B preferably have a different type of glycosidic linkage, a different degree of polymerisation and/or a different monosaccharide composition.

According to a preferred embodiment of the present invention, the percentage of a particular monosaccharide in non-digestible oligosaccharide A is at least 40 number % higher than the percentage of the same monosaccharide in non-digestible oligosaccharide B, preferably at least 50%, more preferably at least 75%, even more preferably at least 90%. An increased diversity of monosaccharides stimulates a wider population of beneficial intestinal bacteria. The percentage of a monosaccharide in the non-digestible oligosaccharide can be simply calculated by dividing the number of the respective monosaccharide units (e.g. glucose) in the non-digestible oligosaccharide by the total number of the monosaccharide units in that non-digestible oligosaccharide and multiply it by 100. When the non-digestible oligosaccharide is a non-digestible oligosaccharide mixture, the contribution of each individual monosaccharide unit in the non-digestible oligosaccharide mixture must be taken into account. The percentage of a monosaccharide in a non-digestible oligosaccharide mixture can simply be determined by completely hydrolysing the mixture and determining the number percentage for each monosaccharide. Preferably non-digestible oligosaccharide A contains at least 40 number % galactose, more preferably at least 67% galactose, more preferably at least 75% galactose. Preferably non-digestible oligosaccharide B contains at least 30 number % fructose, more preferably at least 67% fructose, even more preferably at least 80% fructose.

According to a preferred embodiment of the present invention, the average DP of non-digestible oligosaccharide A is at least 5 monosaccharide units lower than the average DP of non-digestible oligosaccharide B, preferably at least 10, even more preferably at least 15. Preferably, non-digestible oligosaccharide A has an average DP of 2-10, more preferably 3-5. Preferably non-digestible oligosaccharide B has an average DP below 200, more preferably 11-60, even more preferably 20-30. Including a non-digestible oligosaccharide with an increased degree of polymerisation reduces the osmotic load, which is advantageous for an infant nutrition and/or improves prebiotic stimulation of the intestinal microbiota also at more distal parts of the colon. The non-digestible oligosaccharide A and B with a different DP may have the same or different monosaccharide composition. Preferably, non-digestible oligosaccharide A and B have a different monosaccharide composition and a different DP.

Preferably at least 80 wt. %, more preferably at least 95 wt. %, most preferably at least 98 wt. % of the cumulative weight of non-digestible oligosaccharide A and B has a DP below 60, more preferably below 40, most preferably below 20. The lower DP advantageously reduces viscosity and increases fermentability of the non-digestible oligosaccharides. Preferably at least 50 wt. %, preferably at least 75 wt. % of the cumulative weight of non-digestible oligosaccharides A and B are non-digestible oligosaccharides with a DP of 2-8. By using a mixture with a high weight percentage of small non-digestible oligosaccharides the fermentability and stimulatory effect on the growth of the lactic acid bacteria and bifidobacteria is increased.

In a further preferred embodiment of the present invention the percentage of at least one glycosidic linkage of non-digestible oligosaccharide A based on total glycosidic linkages of non-digestible oligosaccharide A is at least 40% higher or lower than the percentage of the same glycosidic linkage in oligosaccharide B, preferably at least 50%, even more preferably at least 75%. The term "glycosidic linkage" as used in the present invention refers to a C—O—C linkage formed between the rings of two cyclic monosaccharides by the elimination of water. An increased diversity in glycosidic linkages stimulates a wider range of beneficial bacteria.

Glycosidic linkages differ in that they covalently bind carbon atoms in the monosaccharide units at differently numbered positions, and/or that they form α or β bonds. Examples of different glycosidic linkages occurring in non-digestible saccharides are β(1,3), α(1,4), β(2,1), α(1,2), and β(1,4) linkages. Preferably the glycosidic linkages in non-digestible oligosaccharide A comprises at least 40% β(1,4) and/or β(1,6) glycosidic linkages, more preferably at least 75%. The glycosidic linkages in non-digestible oligosaccharide B preferably comprise at least 40% β(2,1) glycosidic linkages, more preferably at least 75%. Preferably, non-digestible oligosaccharide A and B differ in monosaccharide unit composition and in type of glycosidic linkage. Preferably, non-digestible oligosaccharide A and B differ in type of glycosidic linkage and DP. Most preferably, non-digestible oligosaccharide A and B differ in type of glycosidic linkage, monosaccharide composition and DP, in order to optimally improve the biodiversity and stimulate the growth of multiple intestinal organisms, especially different species of *Bifidobacterium*.

Preferably at least 60%, more preferably at least 75% even more preferably 90%, most preferably 98% of the total monosaccharide units of non-digestible oligosaccharide A and B are monosaccharides selected from the group consisting of galactose (gal), fructose (fru) and glucose (glu) monosaccharides.

Non-digestible oligosaccharide A is preferably an oligosaccharide selected from the group consisting of β-galacto-oligosaccharide, α-galacto-oligosaccharide, and galactan. According to a more preferred embodiment non-digestible oligosaccharide A is β-galacto-oligosaccharide or transgalacto-oligosaccharide. Preferably non-digestible oligosaccharide A comprises galacto-oligosaccharides with β(1,4) and/or β(1,6) glycosidic bonds and a terminal glucose. Transgalacto-oligosaccharide is for example available under the trade name VIVINAL GOS® (Borculo Domo Ingredients, Zwolle, Netherlands), BI2MUNO® (Clasado), CUP-OLIGO® (Nissin Sugar) and OLIGOMATE55® (Yakult).

Non-digestible oligosaccharide B is preferably fructo-oligosaccharide. A fructo-oligosaccharide may in other context have names like fructopolysaccharides, oligofructose, polyfructose, polyfructan, inulin, levan and fructan and may refer to oligosaccharides comprising β-linked fructose units, which are preferably linked by β(2,1) and/or β(2,6) glycosidic linkages, and a preferable DP between 2 and 200. Preferably, the fructo-oligosaccharide contains a terminal β(2,1) glycosidic linked glucose. Preferably, the fructo-oligosaccharide contains at least 7 β-linked fructose units. In a further preferred embodiment inulin is used as non-digestible oligosaccharide B. Inulin is a type of fructo-oligosaccharide wherein at least 75% of the glycosidic linkages are β(2,1) linkages Typically, inulin has an average chain length between 8 and 60 monosaccharide units. A suitable fructo-oligosaccharide for use in the compositions of the present invention is commercially available under the trade name RAFTILINE HP® (Orafti). Other suitable sources are RAFTILOSE® (Orafti), FIBRULOSE® and FIBRULINE® (Cosucra) and FRUTAFIT® and FRUTALOSE® (Sensus).

Most preferred is transgalacto-oligosaccharide with an average DP below 10, preferably below 6 as non-digestible oligosaccharide A and a fructo-oligosaccharide with an average DP above 7, preferably above 11, even more preferably above 20, as non-digestible oligosaccharide B, since such a combination was found to be optimal for improving intestinal microbiota.

If the composition comprises non-digestible oligosaccharide A and B, the weight ratio non-digestible oligosaccharide A to non-digestible oligosaccharide B is preferably from 1/99 to 99/1, more preferably from 1/19 to 19/1, even more preferably from 1 to 19/1. This weight ratio is particularly advantageous when non-digestible oligosaccharide A has a low DP and non-digestible oligosaccharide B has a relatively high DP. It ensures an optimal equilibrium between osmolality and fermentability. It also ensures an optimal effect of the diversity in monosaccharide composition, glycosidic linkages and/or degree of polymerization. Preferably oligosaccharide A is a transgalacto-oligosaccharide and oligosaccharide B is a fructo-oligosaccharide Thus according to one embodiment of the present infant nutrition comprises the non-digestible oligosaccharides A and B, wherein the non-digestible oligosaccharides A and B differ either:

i) in the percentage of at least one monosaccharide of oligosaccharide A based on total monosaccharide units of oligosaccharide A, the monosaccharide being at least 40 number % higher that the percentage of the same monosaccharide in oligosaccharide B; and/or ii) in the percentage of at least one glycosidic linkage of oligosaccharide A based on total glycosidic linkages of oligosaccharide A, the glycosidic linkage being at least 40% higher than the percentage of the same glycosidic linkage in oligosaccharide B; and/or iii) in the degree of polymerisation of oligosaccharide A, degree of polymerisation of oligosaccharide A being at least 5 monosaccharide units lower than the degree of polymerisation of oligosaccharide B.

In a preferred embodiment the present composition further comprises a non-digestible oligosaccharide C. The non-digestible oligosaccharide C comprises uronic acid oligosaccharides. The term uronic acid oligosaccharide as used in the present invention refers to an oligosaccharide wherein at least 50 number % of the monosaccharide units present in the oligosaccharide is one selected from the group consisting of guluronic acid, mannuronic acid, galacturonic acid, iduronic acid, riburonic acid and glucuronic acid. In a preferred embodiment the uronic acid oligosaccharide comprises at least 50 number % galacturonic acid based on total uronic acid units in the uronic acid oligosaccharide. The uronic acid oligosaccharides used in the invention are preferably prepared from degradation of pectin, pectate, alginate, chondroitine, hyaluronic acids, heparine, heparane, bacterial carbohydrates, and/or sialoglycans, more preferably of pectin and/or alginate, even more preferably of pectin, most preferably polygalacturonic acid. Preferably the degraded pectin is prepared by hydrolysis and/or beta-elimination of fruit and/or vegetable pectins, more preferably apple, citrus and/or sugar beet pectin, even more preferably apple, citrus and/or sugar beet pectin degraded by at least one lyase.

Preferably the present composition comprises between 25 and 100 wt. %, more preferably between 50 and 100 wt. % uronic acid oligosaccharide with a DP of 2 to 250 based on total weight of uronic acid oligosaccharide in the composition, more preferably a DP of 2 to 100, even more preferably a DP of 2 to 50, most preferably a DP of 2 to 20 based on total weight of uronic acid oligosaccharide in the composition.

In a preferred embodiment, at least one of the terminal hexuronic acid units of the uronic acid oligosaccharide has a double bond. The double bond effectively protects against attachment of pathogenic bacteria to intestinal epithelial cells. This is advantageous for infants. Preferably one of the terminal hexuronic acid units comprises the $C_4$-$C_5$ double bond. The double bond at terminal hexuronic acid unit can for example be obtained by enzymatic hydrolysis of pectin with lyase.

The uronic acid oligosaccharide can be derivatised. The uronic acid oligosaccharide may be methoxylated and/or amidated. In one embodiment the uronic acid oligosaccharides are characterized by a degree of methoxylation above 20%, preferably above 50% even more preferably above 70%. As used herein, "degree of methoxylation" (also referred to as DE or "degree of esterification") is intended to mean the extent to which free carboxylic acid groups contained in the uronic acid oligosaccharide have been esterified (e.g. by methylation).

Preferably the composition comprises the non-digestible oligosaccharides transgalacto-oligosaccharide, fructo-oligosaccharide and a pectin degradation product. The weight ratio transgalacto-oligosaccharide:fructo-oligosaccharide:pectin degradation product is preferably (20 to 2):1:(1 to 3), more preferably (12 to 7): 1:(1 to 2).

The present composition preferably comprises 0.05 to 20 wt. % non-digestible oligosaccharide (A+B+C), more preferably 0.5 to 15 wt. %, even more preferably 1 to 10 wt. %, most preferably 2.0 to 10 wt. % based on dry weight of the present composition.

Formulae

The present infant and/or toddler nutrition is preferably enterally administered, more preferably orally. The present infant and/or toddler nutrition is preferably used as an infant formula. The present infant and/or toddler nutrition can advantageously be applied as a complete nutrition for infants. Such food preferably comprises lipid, protein and carbohydrate and is preferably administered in liquid form. Preferably the composition is a ready-to-use liquid food, e.g. is in a ready-to-feed liquid form. A packed ready-to-use liquid food advantageously involves less steps for preparation than a powder to be reconstituted and hence a reduced chance on contamination by harmful micro-organisms.

Hence, the present invention also relates to an infant and/or toddler nutrition which preferably comprises between 5 and 50 en % lipid, between 5 and 50 en % protein, between 15 and 90 en % carbohydrate and non-viable B. breve and non-digestible oligosaccharide A and/or B and optionally C. Preferably the present infant and/or toddler nutrition comprises between 35 and 50 en % lipid, between 7.5 and 12.5 en % protein and between 35 and 80 en % carbohydrate (en % is short for energy percentage and represents the relative amount each constituent contributes to the total caloric value of the preparation).

Preferably the infant and/or toddler nutrition comprises lipids. Preferably the infant and/or toddler nutrition comprises vegetable lipids. Preferably the lipid component is a combination of vegetable lipids and at least one oil selected from the group consisting of fish, animal, algae and bacterial oil. Preferably, the lipid comprises over 50 mg/100 kcal (preferably over 1 wt. % based on total fatty acids) α-linolenic acid (ALA). Preferably the lipid composition has a wt/wt ratio of linoleic acid (LA) and ALA between 4 and 15, more preferably between 5 and 8. Preferably the present infant and/or toddler nutrition comprises long chain polyunsaturated fatty acids (LC-PUFA), more preferably eicosapentaenoic acid (EPA) and/or docosahexaenoic acid (DHA), and/or arachidonic acid (ARA). Preferably the infant and/or toddler nutrition comprises, based on total fatty acids, 0.03 to 0.8 wt. %, more preferably 0.12 to 0.4 wt. % DHA. Preferably the composition comprises, based on total fatty acids, 0.01 to 0.2 wt. %, more preferably 0.03 to 0.1 wt. % EPA. Preferably the composition comprises 0.03 to 1.6 wt. %, more preferably 0.12 to 0.8 wt. % ARA based on total fatty acids. The presence of LC-PUFA advantageously reduces intestinal permeability or improves the immune system or both, thereby exerting a synergistic effect with the other components of the invention regarding an effect against allergy, atopic dermatitis, infections and the like.

Preferably the infant and/or toddler nutrition comprises proteins. The proteins used in the nutritional preparation are preferably selected from the group consisting of non-human animal proteins (such as milk proteins, including caseins and whey proteins, meat proteins and egg proteins), vegetable proteins (such as soy protein, wheat protein, rice protein, potato protein and pea protein), hydrolysates (partially and/or extensively), free amino acids and mixtures thereof. Cow milk derived nitrogen source, particularly cow milk protein proteins such as casein and whey proteins are particularly preferred, as the amino acid composition of these proteins is well balanced. As the present composition is suitably used to reduce the allergic reaction in an infant and/or toddler, the protein of the infant nutrition is preferably selected from the group consisting of hydrolysed milk protein (e.g. hydrolysed casein and/or hydrolysed whey protein), hydrolysed vegetable protein and/or amino acids. The use of these proteins further reduces the allergic reactions of the infant and/or toddler and/or increases protein absorption. Preferably the protein source is extensively and/or partially hydrolysed. More preferably the protein source is extensively hydrolysed whey protein derived from cow's milk.

Preferably the infant and/or toddler nutrition comprises digestible carbohydrates. The digestible carbohydrates used in the nutritional preparation are preferably selected from the group consisting of sucrose, lactose, maltose, galactose, glucose, fructose, corn syrup solids, starch and maltodextrins, and mixtures thereof, more preferably lactose.

The present infant and/or toddler nutrition preferably comprises minerals, trace elements and vitamins, choline, taurine, carnitine, myo-inositol and/or mixtures thereof. Preferably the present composition contains taurine, which reduces the symptoms of asthma (*Adv. Exp. Med. Biol.* 2003 526:403-10). The taurine acts synergistically with the components in the present infant and/or toddler nutrition. Preferably the present infant and/or toddler nutrition comprises nucleotides. Preferably, the composition comprises cytidine 5'-monophospate, uridine 5'-monophospate, adenosine 5'-monophospate, guanosine 5'-monophospate, and inosine 5'-monophospate. Preferably the present infant and/or toddler nutrition comprises 0.005 to 0.07, more preferably 0.01 to 0.035 wt. % nucleotides based on dry weight. The presence of nucleotides advantageously affects the immune system, intestinal barrier and/or intestinal microbiota. Thereby nucleotides are expected to exert a synergistic effect with the other components of the invention regarding an effect against allergy, atopic dermatitis, infections and the like. Preferably the present infant and/or toddler nutrition comprises both LC-PUFA and nucleotides.

Preferably, the present infant and/or toddler nutrition is a non fermented composition. Fermentation by micro-organisms results in a lowering of the pH, which may be disadvantageous for newly formed teeth. Preferably, the composition has a pH above 5.5, more preferably 6.0, even more preferably 6.5 in order to reduce damage to teeth. Preferably the infant and/or toddler nutrition has a pH between 6 and 8.

Preferably, the present infant and/or toddler nutrition is a fermented composition. Preferably the present nutrition comprises a milk-derived product fermented by *Bifidobacterium breve*, of which the cells are inactivated after fermentation. The milk derived product which has been fermented by *B. breve* comprises fragments or/and products excreted *B. breve*, such as glycoproteins, glycolipids, peptidoglycan, lipoteichoic acid (LTA), lipoproteins, capsular polysaccharides, and/or DNA. These immunogenic molecules induce the tolerance of the intestinal tract against colonisation with lactic acid producing bacteria. Furthermore, upon fermentation and/or other interactions of *B. breve* with the milk-derived products, additional bio-active compounds may be formed, such as bioactive peptides and/or oligosaccharides, which also stimulate the immune system and/or stimulate the colonization of the intestinal microbiota. The milk derived product is preferably selected from the group consisting of milk, casein, casein protein, casein protein hydrolysate, casein peptides, whey, whey protein, whey protein hydrolysate, whey peptides, and lactose or mixtures thereof. Milk can be whole milk, semi-skimmed milk and/or skimmed milk. Whey can be sweet whey, and/or acid whey. Preferably the aqueous substrate to be fermented is skimmed milk.

Stool irregularities (e.g. hard stools, insufficient stool volume, diarrhoea) is a major problem in many babies. It was found that stool problems may be reduced by administering the present combination of non-viable *B. breve* and a non-digestible oligosaccharide in liquid food which has an osmolality between 50 and 500 mOsm/kg, more preferably between 100 and 400 mOsm/kg.

In view of the above, it is also important that the liquid food composition does not have an excessive caloric density, however still provides sufficient calories to feed the subject. Hence, the liquid food preferably has a caloric density between 0.1 and 2.5 kcal/ml, even more preferably a caloric density of between 0.4 and 1.2 kcal/ml, most preferably between 0.55 and 0.75 kcal/ml.

The present infant and/or toddler nutrition preferably has a viscosity between 1 and 60 mPa·s, preferably between 1 and 20 mPa·s, more preferably between 1 and 10 mPa·s, most preferably between 1 and 6 mPa·s. The low viscosity ensures a proper administration of the liquid, e.g. a proper passage through the hole of a nipple. Also this viscosity closely resembles the viscosity of human milk. Furthermore, a low viscosity results in a normal gastric emptying and a better energy intake, which is essential for infants and/or toddlers which need the energy for optimal growth and development. The present composition is preferably prepared by admixing a powdered composition comprising with water. Normally infant formula is prepared in such way. The present invention thus also relates to a packaged power composition wherein said package is provided with instruction to admix the powder with a suitable amount of liquid, thereby resulting in a liquid composition with a viscosity between 1 and 60 mPa·s.

The viscosity of the liquid is determined using a Physica Rheometer MCR 300 (Physica Messtechnik GmbH, Ostfilden, Germany) at shear rate of 95 $s^{-1}$ at 20° C.

Including non-viable *B. breve* increases the shelf-life of infant and/or toddler nutrition in particular compared to infant and/or toddler nutrition comprising viable *B. breve*. This is particularly advantageous for liquid infant and/or toddler nutrition. Thus the infant and/or toddler nutrition according to the present invention preferably is shelf stable at ambient temperature for at least 6 months, preferably at least 12 months, preferably when the infant and/or toddler nutrition is in a liquid, ready-to-feed form.

Applications

The infant and/or toddler nutrition according to the present invention has been found to be particularly useful as a nutrition for prematurely born babies, maturely born babies (vaginally as well as caesarean section delivered infants), infants which are in the adaptation period to solid food, infants and/or toddlers with an increased risk for or suffering from allergy, and/or infants and/or toddlers with an increased risk for infections, such as infants and/or toddlers attending day care centres, or suffering from infections. The invention is particularly advantageous for vaginally born infants. The invention is particularly advantageous for caesarean section delivered infants since these infants have an impaired microbial colonisation of the large intestine.

Hence the present invention provides a method for providing nutrition to a human infant and/or toddler, said method comprising administering to the infant and/or toddler the present composition. Preferably the infant and/or toddler has an age between 0 and 36 month, even more preferably between 0 and 18 month, most preferably between 0 and 12 months. In a preferred embodiment the present invention provides a method for providing nutrition to a human infant with the age of 0-12 months. In a preferred embodiment the present invention provides a method for providing nutrition to a human toddler with the age of 12-36 months.

The present invention also provides a method for stimulating the health of an infant and/or toddler, comprising administering a composition comprising non-viable *B. breve* and a non-digestible oligosaccharide A and/or B and optionally C to the infant and/or toddler.

The present invention thus also provides a method for stimulating the health in an infant and/or toddler comprising the steps a) admixing i) an in particular nutritionally or pharmaceutically acceptable liquid; and ii) a dry composition, wherein the dry composition II comprises *B. breve* and a non-digestible oligosaccharide A and/or B and optionally C, and step b) administering the composition obtained in step a) to an infant and/or toddler.

Administration of an infant nutrition comprising non-viable *B. breve* and a non-digestible oligosaccharide advantageously results in improvement of the intestinal microbiota by increasing the numbers of lactic acid producing bacteria and/or by decreasing the numbers of pathogenic bacteria and/or by stimulation of the immune system. Preferably, an infant and/or toddler nutrition comprising non-viable *B. breve* and non-digestible oligosaccharide A and/or B and optionally C is used in a method for treatment and/or prevention of gastro-intestinal disorders and/or immune disorders in infants and/or toddlers, said method comprising administering said composition to an infant and/or toddler.

Particularly allergy (more particularly food allergy), allergic rhinitis, food hypersensitivity, atopic dermatitis, i.e. allergic or atopic eczema, particularly itchy skin caused by dermatitis, allergic conjunctivitis, asthma, particularly wheezing caused by asthma, diarrhoea, intestinal inflammation, infections, constipation, intestinal cramps and/or colics, can be suitably treated with the present nutrition. In a preferred embodiment, the present invention provides a method for the treatment and/or prevention of (food) allergy, allergic rhinitis, food hypersensitivity, eczema (i.e. atopic dermatitis), asthma, diarrhoea, intestinal inflammation, and/or infection. Preferably the present invention provides a method for the treatment and/or prevention of infection and/or diarrhoea. In a preferred embodiment, the present invention provides a method for the treatment and/or prevention of (food) allergy, asthma and/or atopic dermatitis. The reduced occurrence of these diseases is due to improved microbiota, improved immune system and/or reduced translocation of allergens through the gut barrier. In one embodiment the composition is used to improve the skin of and reduce the itch of the skin in an infant and/or toddler. In one embodiment the composition is used to reduce wheezing in an infant and/or toddler.

Furthermore, administration of an infant and/or toddler nutrition comprising non-viable *B. breve* and a non-digestible oligosaccharide strengthens the immune system. In one embodiment, an infant and/or toddler nutrition comprising non-viable *B. breve* and a non-digestible oligosaccharide A and/or B and optionally C is used in a method for treatment or prevention of systemic and/or respiratory infections and/or inflammation in infants and/or toddlers, said method comprising administering said infant nutrition to an infant and/or a toddler.

Preferably an infant and/or toddler nutrition comprising non-viable *B. breve* and a non-digestible oligosaccharide A and/or B and optionally C is used in a method for treatment or prevention of diaper dermatitis (or diaper rashes, nappy rashes, nappy dermatitis), in infants and/or toddlers, said method comprising administering said infant nutrition to an infant and/or a toddler.

Preferably an infant and/or toddler nutrition comprising non-viable *B. breve* and a non-digestible oligosaccharide A and/or B and optionally C is used in a method for treatment or prevention of colic and/or abdominal cramps, abdominal bloating, flatulence, abdominal pain, constipation, inflammatory bowel disease, irritable bowel syndrome, and/or for improvement of bone mineralisation, and/or prevention of obesity later-in-life (particularly central obesity), in infants and/or toddlers, said method comprising administering said infant nutrition to an infant and/or a toddler.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

EXAMPLES

Example 1

Non-Viable *B. breve* has an Anti-Allergic Effect

Male BALB/c mice (6-8 weeks) were obtained from Charles River (Someren, The Netherlands). Mice were housed individually in type II cages with semi-synthetic food (AING93) based on the growth formulation of the American Institute of Nutrition (1993) and water both provided ad libitum. The mice were divided into the different treatment groups A-D (N=6) and each group was divided in two cohorts of 3 animals per cohort. The second cohort started with a delay of one week.

Active sensitization was performed by two intraperitoneal injections at day 0 and day 7. The mice from the negative control group (group A) were sensitized with phosphate buffered saline (PBS) containing 2.25 mg aluminum hydroxide and 2.25 magnesium hydroxide as adjuvant (Alum inject, Pierce) in a volume of 100 µl by i.p. injection. Mice from the other groups were sensitized with 10 µg ovalbumin (OVA) in PBS (0.2 µm filtered) containing 2.25 mg aluminum hydroxide and 2.25 mg magnesium hydroxide (Alum Imject, Pierce) in a volume of 100 µl by i.p. injection.

Four weeks after the last injection (on day 35, 38 and 41), the mice from groups B, C, and D were exposed for 20 minutes to aerosolised ovalbumin (10 mg/ml) (totally 3 times one aerosol for 20 minutes). Mice from group A were exposed to aerosolised saline. The aerosols were generated with a Jet nebulizer (Pari IS-2, Pari-Werk GmbH, Starnberg, Germany, particle size 2-3 microns) connected to a macrolon cage in which the mice were placed.

Starting on day 28 and ending on day 42, mice were treated orally every day: Mice from group A and B received 200 µl NaCl/day. Mice from group C received $10^9$ CFU *Bifidobacterium breve* M16-V in 200 µl saline and mice from group D received the same amount of bacteria as in group C with the difference that it was heat-inactivated for 10 minutes at 90° C. Composition C comprised less than $10^3$ cfu living *B. breve* per g dry weight (i.e. below the detection limit). Composition C comprised inactivated *B. breve* in an amount equivalent to $10^9$ cfu *B. breve*.

At day 41 basal ear thickness was determined using a spring-loaded caliper (Mitutoyo, Veenendaal, The Netherlands). Subsequently, mice were challenged by injecting 20 µl OVA (40 µg/ml in PBS) intracutaneously into the ear pinnea of both ears after animals had been anaesthetized by isoflurane, $O_2$ and $N_2O$. Duplo measurements of both ears were taken before and 1, 6 and 24 hours after OVA challenge under anesthetization of the animals The results are shown in table 1.

The negative control showed an ear thickness increase of about 20% compared to the positive control, which was set to 100%. Treatment with viable *B. breve* showed only a 45% increase of ear thickness. This indicates a reduction of the allergic reaction of about 70% compared to the positive and negative control. Non-viable *B. breve* resulted in a 60% increase of ear thickness. This indicates a reduction of the allergic reaction of about 52% compared to the positive and negative control. These results are indicative of an anti-allergic and/or immune improving effect of non-viable *B. breve* to a comparable extent (about 75%) of viable *B. breve* cells. This is surprising since the inactivated *B. breve* is not expected to have such an effect since it cannot have an effect via improvement of the flora.

TABLE 1

Percentage of ear thickness increase due to allergic reaction to ovalbumin in balb/c mice.

| Mice treatment group | Relative ear increase in % (s.e.) | Relative reduction in allergic reaction in % |
|---|---|---|
| Group A, Negative control | 20.49 (9.83) | 100 |
| Group B, Positive control | 100 (6.86) | 0 |
| Group C, treatment with living *B. breve* | 45.13 (8.64)* | 69 |
| Group D, treated with non-viable *B. breve* | 58.60 (13.12)* | 52 |

*p < 0.05 compared to positive control.

Example 2

The Combination of Non-Viable *B. breve* and Non-Digestible Oligosaccharides has an Enhanced Anti-Allergic Effect Compared to the Single Components C3H/HeOuJ mice (3-5 weeks) were obtained from Charles River. Mice were housed individually in type II cages with semi-synthetic cow's milk protein free food and water both provided ad libitum. The mice were divided into the different treatment groups A-E (N=6) for 2 weeks. The different treatment groups A-E (N=6) were a negative control group (group A), a positive control group (Group B), a group receiving 2*10$^9$ CFU *Bifidobacterium breve* M16-V, heat-inactivated for 10 minutes at 90° C., per g diet (group C), a group receiving 20 mg non-digestible oligosaccharides (TOS (derived from VIVINAL GOS®, Borculo Domo) and 1cFOS (RAFTILINEHP®, Orafti) in a w/w/ratio 9/1 per g diet (Group D), and a group receiving both heat inactivated *B. breve* and non-digestible oligosaccharides (Group E). The diet of group C and D comprises thus inactivated *B. breve* in an amount equivalent to 2*10$^9$ CFU per g diet. The composition comprises less than 1 10$^3$ cfu living *B. breve*/g diet (which is below the detection limit).

Active sensitization was performed by intragastric gavage at day 14, 21, 28, 35, 42 and 49 with 0.5 ml whey protein (DMV International, Veghel, 40 mg whey protein/ml PBS, with cholera toxin, 20 μg/ml PBS, as an adjuvant.) The mice from the negative control group (group A) were sensitized with PBS (phosphate buffered saline) containing cholera toxin as adjuvant.

On day 54, the mice from groups A, B, C, D and E were challenged with intradermally injection of 20 μl whey protein (0.5 mg protein/ml PBS) in the left ear pinnae. In the right ear as a control PBS was injected. Ear thickness was measured in duplicate using a digital micrometer (Mitutuyo, Veenendaal) at t=0 and t=1. The t=0 and control right ear swelling was subtracted from the thickness measured in the left ear at t=1.

The results are shown in table 2. The negative control showed an ear thickness increase of 36.0 μm (set to 0%) compared to the positive control, 159.9 μm, which was set to 100%. Treatment with non-viable *B. breve* showed only an increase of ear thickness of 116.0 μm. This indicates a reduction of the allergic reaction of about 35% compared to the positive and negative control. The use of non-digestible oligosaccharides resulted in a 103.8 μm increase of ear thickness. This indicates a reduction of the allergic reaction of about 45% compared to the positive and negative control. The combination of non-viable *B. breve* and non-digestible oligosaccharides resulted in an increase of ear thickness of only 80.4. This indicates an unexpected improved reduction of allergic reaction of 64% compared to the positive and negative control.

TABLE 2

Mean ear thickness increase due to allergic reaction to whey protein in mice.

| Mice treatment group | Ear increase in μm (s.e.) | Relative reduction in allergic reaction in % |
|---|---|---|
| Group A, Negative control | 36.0 (5.7)* | 100 |
| Group B, Positive control | 159.9 (12.2) | 0 |
| Group C, treatment with non-viable *B. breve* | 116.0 (12.2)* | 35 |
| Group E, treated with non-viable *B. breve* and prebiotics | 80.4 (10.8)* | 64 |

*p < 0.05 compared to positive control.

These results are indicative for an unexpected improved effect the combination of non-digestible oligosaccharides and non-viable *B. breve* compared to the single components. This is unexpected, since the inactivated *B. breve* cannot metabolize the non-digestible oligosaccharides.

Example 3

Liquid Toddler Milk with *B. breve*

A liquid, ready-to drink, growing up milk comprising per 100 ml:

67 kcal
1.9 g protein (cow's milk protein)
8.1 g digestible carbohydrates (of which 7.8 g lactose)
3.0 g fat
0.8 g non-digestible oligosaccharides:
0.72 galacto-oligosaccharides derived from Vivival GOS
0.08 g fructan derived from RAFTILINEHP®
5.10$^9$ cfu equivalent of heat non-viable *Bifidobacterium breve* pH about 6.7

The invention claimed is:

1. A method for treating and/or reducing the occurrence of an allergic disease or condition in an infant or toddler subject, comprising feeding to the subject a nutritional composition which has a pH between 5.5 and 8 and which comprises:
    (a) a first and a second non-digestible oligosaccharide each having a degree of polymerization of 2 to 200, wherein the first non-digestible oligosaccharide is a transgalacto-oligosaccharide and the second non-digestible oligosaccharide is a fructo-oligosaccharide;
    (b) non-viable *Bifidobacterium breve* bacteria from strain M-16V or I-2219 in an amount equivalent to 10$^6$ to 10$^{13}$ viable colony forming units (cfu) per gram dry weight of the nutritional composition, wherein viable *Bifidobacterium breve* bacteria are present in an amount that is below their detection limit as measured by plating; and
    (c) cow's milk protein.

2. The method according to claim 1 wherein the allergy is a food allergy.

3. The method according to claim 1, wherein the nutritional composition is in liquid form.

4. The method according to claim 1, wherein the cow's milk protein is hydrolyzed.

5. The method according to claim 1, wherein the nutritional composition is not fermented.

6. The method according to claim 1, wherein the weight ratio of the first oligosaccharide to the second oligosaccharide is from 19/1 to 1/19.

7. The method according to claim 1, wherein the nutritional composition comprises 0.5 to 10 wt. % non-digestible oligosaccharide based on dry weight of the nutritional composition.

8. The method according to claim 1 wherein the nutritional composition further comprises eicosapentaenoic acid and/or docosahexaenoic acid, and/or arachidonic acid.

9. The method according to claim 1 wherein the nutritional composition further comprises between 5 and 50 energy % lipid, between 5 and 50 energy % protein, and between 15 and 90 energy % carbohydrate.

10. The method according to claim 1 wherein the degree of polymerization of the first oligosaccharide is at least 5 monosaccharide units less than the degree of polymerization of said second oligosaccharide.

11. The method according to claim 1, wherein the non-viable *Bifidobacterium breve* are produced by inactivating viable *Bifidobacterium breve* using heat treatment.

* * * * *